United States Patent [19]
Kalmanovitch

[11] Patent Number: 5,271,674
[45] Date of Patent: Dec. 21, 1993

[54] APPARATUS AND METHOD FOR PREDICTING ASH DEPOSITION ON HEATED SURFACES OF A FUEL BURNING COMBUSTION VESSEL

[75] Inventor: David P. Kalmanovitch, Worcester, Mass.

[73] Assignee: Riley Storker Corporation, Worcester, Mass.

[21] Appl. No.: 994,338

[22] Filed: Dec. 21, 1992

[51] Int. Cl.$^5$ .............................. G01N 25/04
[52] U.S. Cl. ........................ 374/16; 374/43; 110/342; 110/165 R
[58] Field of Search ............ 374/16, 17, 18, 19, 374/21, 43, 45, 160; 110/165 R, 185, 186, 341, 342, 343, 344, 349

[56] References Cited

U.S. PATENT DOCUMENTS

| | | | |
|---|---|---|---|
| 4,038,188 | 7/1977 | May, Sr. et al. | 110/342 |
| 4,046,509 | 9/1977 | Bäckerud | 374/25 |
| 4,159,876 | 7/1979 | Egan et al. | |
| 4,166,421 | 9/1979 | Stribling | |
| 4,377,118 | 3/1983 | Sadowski | 110/343 |
| 4,722,610 | 2/1988 | Levert et al. | 374/43 |
| 4,927,270 | 5/1990 | Bonnard | 374/16 |
| 4,953,481 | 9/1990 | Clayton | 110/342 |
| 4,969,408 | 11/1990 | Archer et al. | 110/343 X |
| 5,158,024 | 10/1992 | Tanaka et al. | 110/185 |

OTHER PUBLICATIONS

Benson, S. A., E. N. Steadman and D. P. Kalmanovitch, "Studies of the Formation of Alkali and Alkaline Earth Aluminosilicates During Coal Combustion Using a Laboratory Scale Furnace", Atlanta, Georgia, Oct. 13-15, 1987.

Kalmanovitch, David P., "A Practical Approach to Predicting Ash Deposition", Riley Stoker Corporation, Worcester, Massachusetts, 1989.

Primary Examiner—William A. Cuchlinski, Jr.
Assistant Examiner—G. Bradley Bennett
Attorney, Agent, or Firm—Mason, Kolehmainen, Rathburn & Wyss

[57] ABSTRACT

Apparatus and method are provided for predicting ash deposition in combustion systems. An ash sample is obtained from a selected fuel under controlled conditions. Chemical composition characteristics of the obtained ash sample are identified by a particle-by-particle analysis of the obtained ash sample. An equilibria phase diagram is determined responsive to the identified characteristics of each particle of the obtained ash sample. Then a eutectic temperature of each the particle of the obtained ash sample is determined utilizing the identified equilibria phase diagram.

10 Claims, 5 Drawing Sheets

APPARATUS AND METHOD FOR PREDICTING ASH DEPOSITION ON HEATED SURFACES OF A FUEL BURNING COMBUSTION VESSEL

BACKGROUND OF THE INVENTION

1. Field of the Invention

The present invention relates generally to combustion systems, and more particularly to an apparatus and method for predicting ash deposition on heated surfaces of a fuel burning combustion vessel in a combustion system to determine operational parameters for the combustion system.

2. Description of the Prior Art

The formation of deposits on heat transfer surfaces in combustion systems such as coal-fired boilers remains a major operating concern. Coal is a major source of fuel for generating electrical power in the United States. Ash species produced from inorganic impurities in coal during combustion that produce deposits on heat transfer surfaces reduce thermal efficiency, cause corrosion and/or erosion of structural material and lead to particulate emissions in excess of current standards.

Despite extensive studies on the fundamental aspects of ash formation and behavior, accurate, dependable and useful models of ash deposition have not been developed. Better methods of predicting ash deposition are needed, particularly for use by the utility industry.

SUMMARY OF THE INVENTION

A principal object of the invention is to provide a method and apparatus for predicting ash deposition on heated surfaces of a fuel burning combustion vessel in a combustion system to determine operational parameters for the combustion system. Other objects are to provide such method and apparatus in which chemical analysis is provided on a particle-by-particle basis together with eutectic temperature determination and to provide such method and apparatus that overcome many of the disadvantages of prior art arrangements.

In brief, the objects and advantages of the present invention are achieved by apparatus and method for predicting ash deposition in combustion systems. An ash sample is obtained from a selected fuel under controlled conditions. Chemical composition characteristics of the obtained ash sample are identified by a particle-by-particle analysis of the obtained ash sample. An equilibria phase diagram is determined responsive to the identified characteristics of each the particles of the obtained ash sample. Then a eutectic temperature of each of the particles of the obtained ash sample is determined utilizing the identified equilibria phase diagram.

BRIEF DESCRIPTION OF THE DRAWING

These and other objects and advantages of the present invention will become readily apparent upon consideration of the following detailed description and attached drawing, wherein.

DETAILED DESCRIPTION OF THE PREFERRED EMBODIMENT

Figure 1:
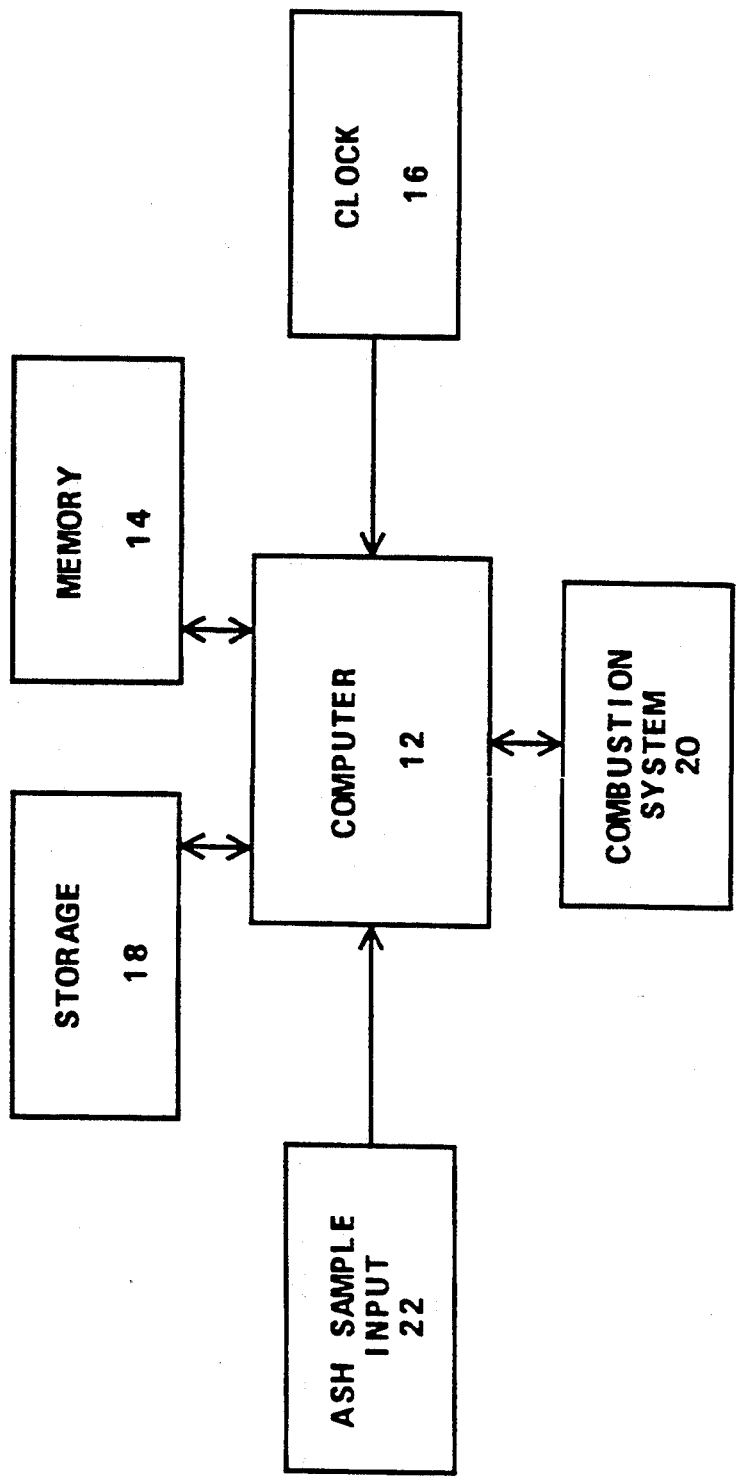
FIG. 1 is a schematic and block diagram of an ash deposition prediction system embodying the present invention.

In FIG. 1 there is shown a partly schematic block diagram of parts of ash deposition prediction system 10 including a controller unit or computer generally designated as 12, a memory 14 for storing program and parameter data, a clock 16 for timing and control and a data storage medium 18 for storing data together with a combustion system 20 utilizing an ash sample input 22 shown applied to the computer 12. System 10 is illustrated in simplified form sufficient for an understanding of the present invention because the utility of the present invention is not limited to the details of a particular construction of the controller computer 12 or combustion system 20. Various commercially available devices can be used for computer 12, for example, such as an AS400 manufactured and sold by International Business Machines Corp. of Armonk, N.Y. Computer 12 is suitably programmed to execute the flowchart of FIG. 2 of the invention. In accordance with a feature of the present invention, a method is provided for predicting ash deposition on heated surfaces of a fuel burning combustion vessel in the combustion system 20 to determine operational parameters for the combustion system utilizing an identified minimum eutectic temperature of the system. The formation of hard-bonded deposits on heat transfer surfaces in combustion systems such as coal-fired boilers is due to the molten nature of the ash particles themselves. In accordance with the method of the invention, phase equilibria data is used to determine the minimum temperature at which a liquid phase will be present.

Figure 2:
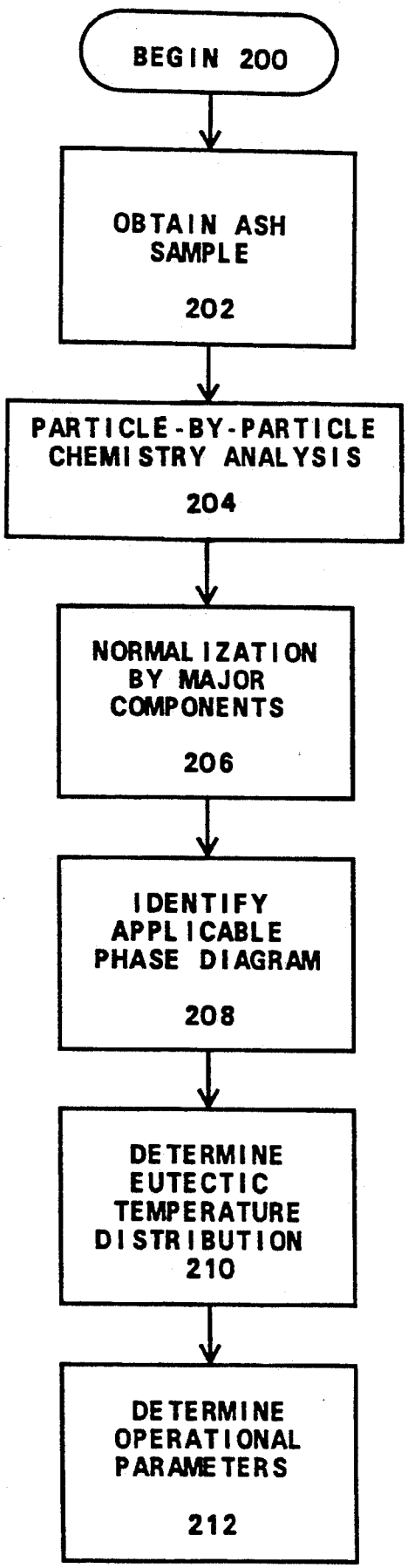
FIG. 2 is a flow chart illustrating sequential steps for providing the ash deposition prediction system of FIG. 1.

Referring now to FIG. 2, there is shown a logic flow chart illustrating sequential operations beginning at a block 200 labelled BEGIN performed by the controller computer 12. First an ash sample is obtained as indicated at a block 202 labelled OBTAIN ASH SAMPLE. The ash sample input 22 to the computer 12 can be any sample produced from a particular fuel; however, the sample should not be a deposit derived from the fuel. An ash sample preferably is obtained via a controlled combustion experiment using proper sampling conditions and by establishing the size fraction. Suitable samples can be obtained from hoppers or a baghouse system located after the convection pass of a boiler in combustion system 20, or from entrained ash sampled on-line during operation of the boiler at known load, for example, sampling at the furnace exit before the convection pass. Also, low-temperature ash samples can be prepared from a particular fuel using oxygen plasma or ash samples derived from a fuel during or after bench-scale or pilot scale testing. Ash can be derived from thermogravimetric analysis or differential gavimetric analysis tests of the fuel. Standard procedures of the American Society for Testing & Materials (ASTM) for production of ash sample under laboratory conditions can be utilized to obtain the ash sample at block 202.

Then chemical composition of individual ash particles is provided instead of bulk ash chemistry as indicated at a block 204 labelled PARTICLE-BY-PARTICLE CHEMISTRY ANALYSIS. Ash samples can be analyzed utilizing various conventional techniques, and the minimum melting point of ash particles is established based on the chemical composition. For example, size distribution analysis techniques include sieve, Coulter counter, Malvern laser and computer controlled scanning electron microscopy (CCSEM). Crystalline phase assemblage analysis can be provided by powder x-ray diffraction. An important feature of the invention is the analysis of the ash samples to obtain the chemical composition of individual particles that comprise the ash system. Chemical composition of individual particles can be provided by electron microprobe analysis-based techniques such as CCSEM and scanning electron microscopy point count (SEMPC). The sample is analyzed using an electron microprobe facility to determine the chemical composition of a large number of individual ash particles, for example, over 200 ash particles.

Next, the chemical composition of the particles is determined as a function of size and normalized as indicated at a block 206 labelled NORMALIZATION BY MAJOR COMPONENTS. The focus of the analysis is on the particle sizes representing about 90% or more of the particles either by weight or by volume. The chemical composition is sorted with respect to known chemical groups and phases. For example, a particle can be classified as a calcium aluminosilicate particle if the only components present in concentrations greater than 5% are Ca, Al and Si. Further analysis can be performed to determine if the chemical composition corresponds to a known crystalline phase present in ash systems.

Then applicable phase diagrams are identified as indicated at a block 208 labelled IDENTIFY APPLICABLE PHASE DIAGRAM before the eutectic temperature of each particle is obtained. The eutectic temperature and eutectic distribution is determined as indicated at a block 210 labelled DETERMINE EUTECTIC TEMPERATURE DISTRIBUTION. The eutectic temperature of each particle is obtained by first determining which equilibrium system best describes the chemical composition at the block 208. Each composition is then used to determine the eutectic temperature using phase equilibria data. This can be done using the relevant 2, 3 or 4 component phase diagrams or a more complex phase equilibria model. The data, which can be represented as a table of normalized chemical composition and eutectic temperatures, can then be analyzed to establish the minimum melting temperatures of the system. Eutectic temperatures are determined by interpolating the chemical composition on a suitable phase equilibrium diagram.

For example, a particle containing calcium and silica will be governed by the equilibrium system $CaO-SiO_2$. Particles present as oxides in the ash system contain at the most four components in significant concentrations. The identified chemical composition of the particle is used to establish where in the phase diagram the particle lies. A computer program labelled ATTACHMENT A, available with the file history and not for publication as part of this patent and written in Fortran and entitled "Eutectic.For", determines which phase diagram to use and determines the eutectic temperature from the phase diagram as illustrated in FIG. 3.

Figure 4:
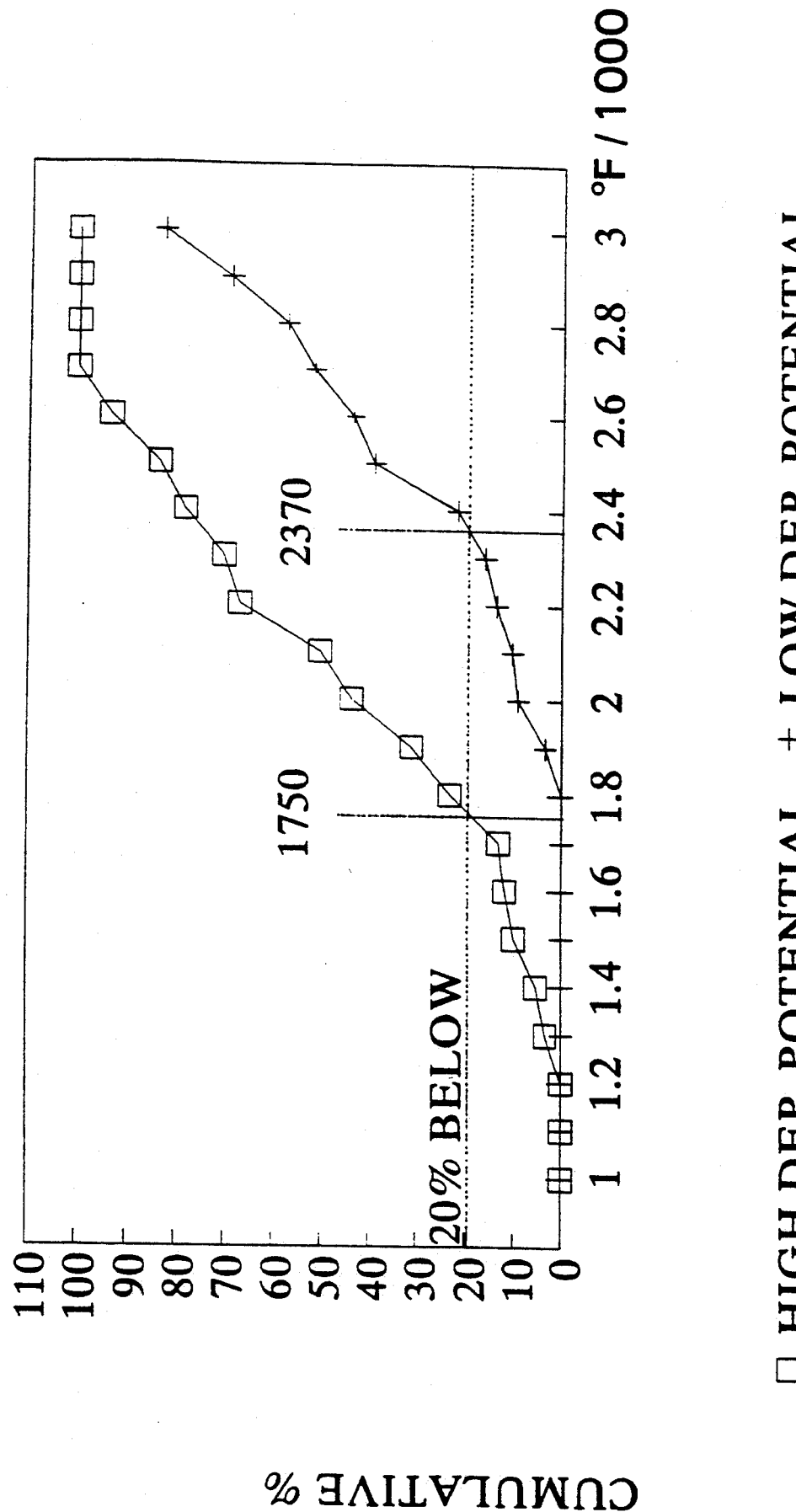
FIGS. 4 and 5 are charts illustrating idealized eutectic distributions comparing high and low deposition potential ashes.
Figure 5:
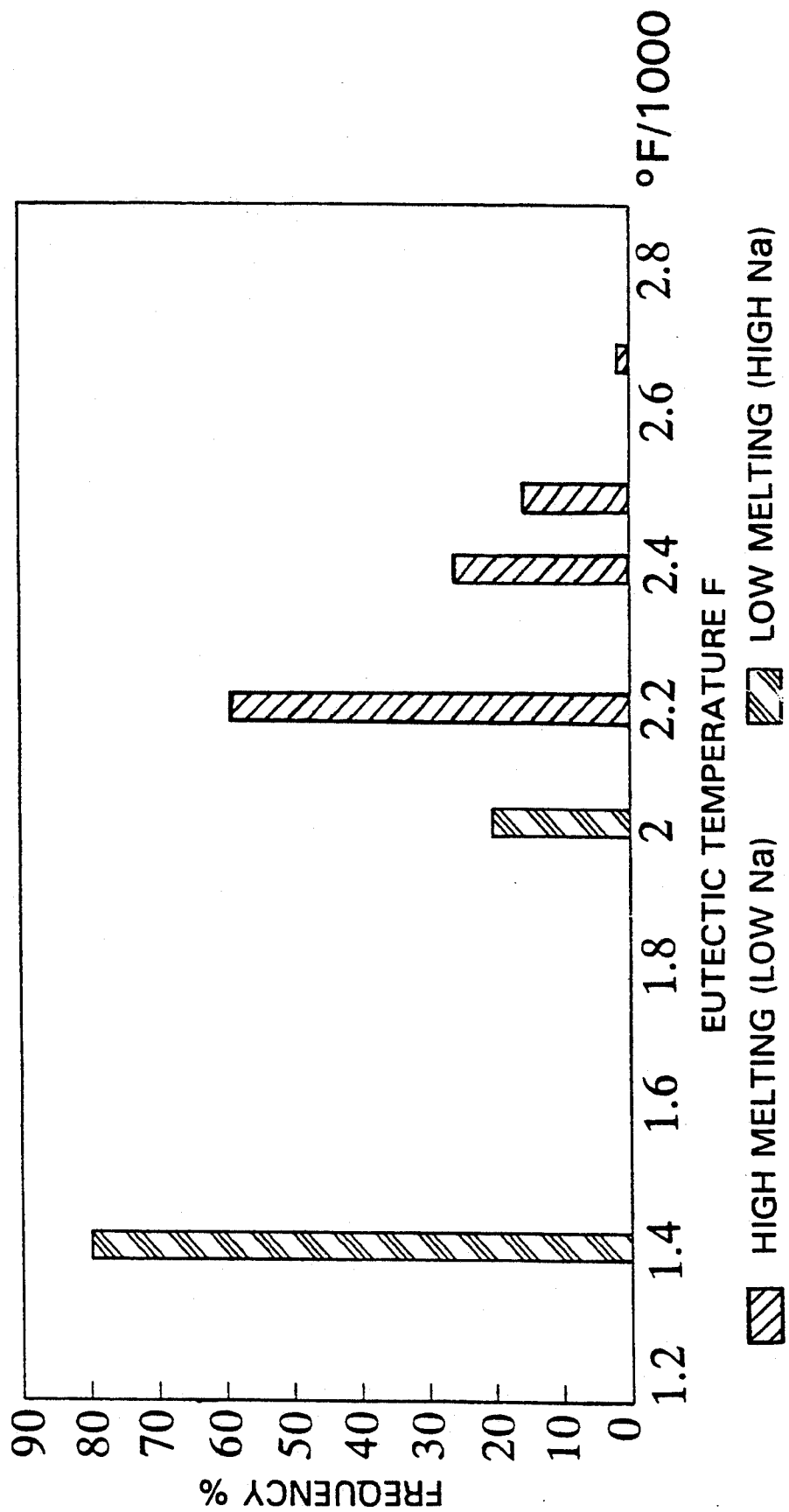

The eutectic temperature of each of the points is then processed statistically to obtain a distribution of the data. The data can be illustrated by a frequency, cumulative % under or similar type of plot as illustrated in FIGS. 4 and 5. The distribution is then used to show the temperature at which the ash system will have less than a given amount of liquid phases. The eutectic temperature and distribution data can then be used to establish gas temperatures and metal temperatures in the fuel burning combustion vessel.

Next, the sequential operations are used to provide specific operating and design conditions including firing rate/load; attemperator operation; excess air levels; sootblower location and operation; and gas temperatures in the convective pass design of fuel blending requirements as indicated at a block 212 labelled DETERMINE OPERATIONAL PARAMETERS. The above operating and design conditions are obtained utilizing the minimum melting temperature of the ash particles formed from the particular fuel, for example the particular coal. Utilizing the identified eutectic temperature distribution at block 210, the lowest temperature at which a liquid phase will be present can be used, for example, to establish an upper gas temperature limit. Also, the amount of particles with eutectics below a given temperature can be used to obtain a measure of the degree of deposition on heat transfer surfaces at a given gas temperature. The nature of the eutectic phases can also be established to determine the effect of the liquid phases predicted on the deposition potential of the ash and rate of growth and development of strength.

Figure 3:
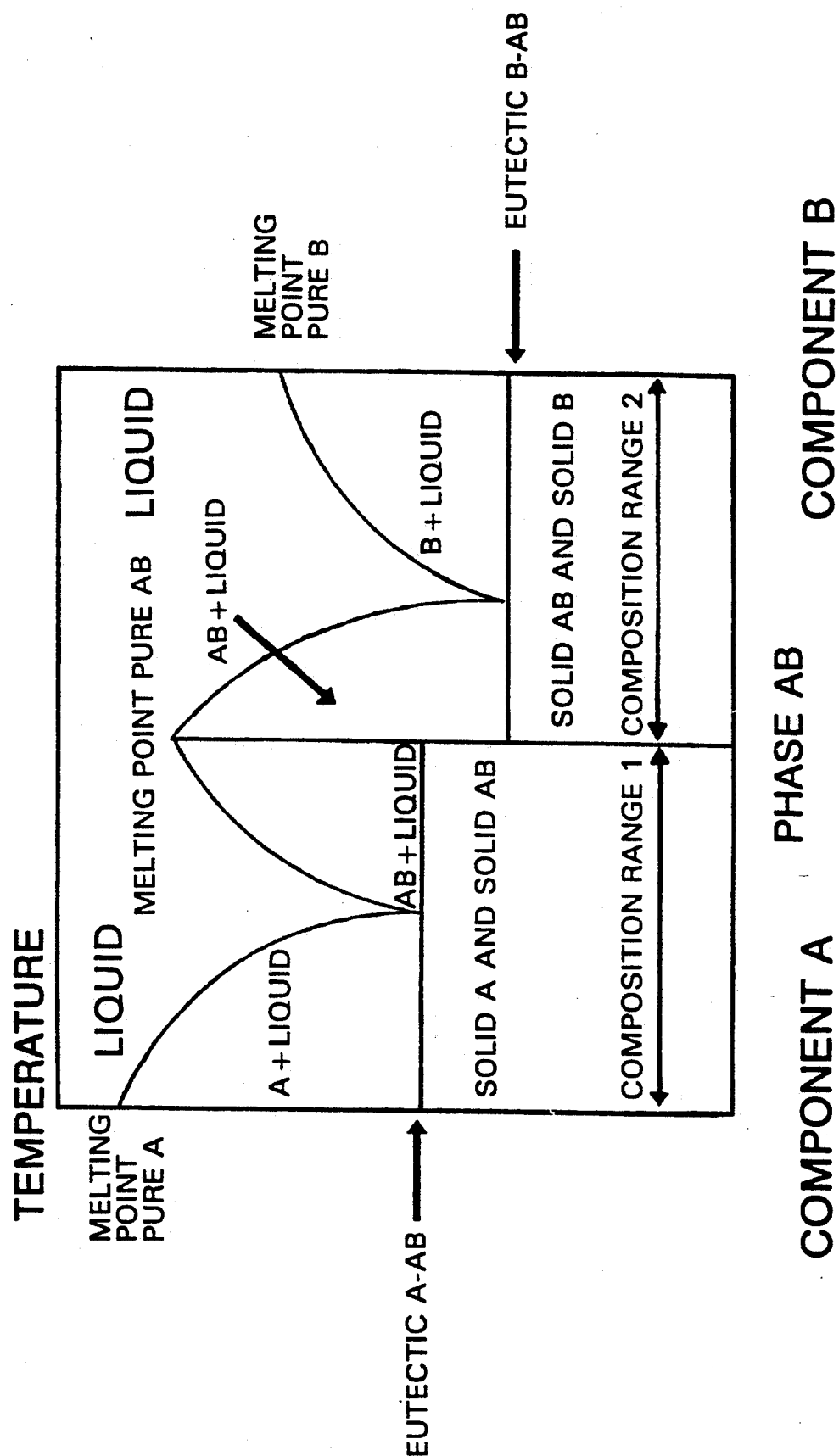
FIG. 3 is a simplified binary phase diagram chart illustrating eutectic (minimum) temperatures of mixtures of components determined in accordance with a method of the invention.

A simplified phase diagram is shown in FIG. 3. Idealized distribution curves and charts for both a low-deposition potential ash and a high deposition potential ash are shown in FIGS. 4 and 5.

Having reference to FIG. 3, the illustrated phase diagram depicts the basis of the technique of determining the eutectic temperature. The phase diagram illustrates a binary system with a compound AB formed as a product of reaction between components A and B. The vertical axis represents temperature. Pure compounds A, B and AB have distinct melting points. However, when in the presence of another component, the melting temperature is reduced. The curves represent the change in melting or liquidus temperature of mixtures of the components as a function of composition. Furthermore, the curves meet at a point called a eutectic or the minimum melting point. This point represents the temperature at which the system will begin to melt when heated and the composition of the liquid phase at the initial melting. Conversely, if the mixture was molten, the eutectic represents the minimum temperature at which a liquid phase will be present. As shown in FIG. 3, phases present at temperatures below the eutectic are solid, for example, the line A-AB is often referred to as the solidus. Therefore, compositions in the illustrated range 1 indicated in FIG. 3 have a minimum melting temperature represented by A-AB and compositions in the illustrated range 2 have a minimum melting temperature represented by the line AB-B.

Each of the FIGS. 4 and 5 provides an example for representing the data. The vertical axis represents percentage levels, cumulative % in FIG. 4, and the horizontal axis represents temperature. For example, FIG. 4 shows the temperatures at which 20% of the particles will have liquid phases for the high deposition potential ash and the low deposition potential ash. It can be seen that the low deposition potential ash will have 20% liquid phases at a much higher temperature than the high deposition potential ash. The 20% level of particles with eutectics below a given temperature is given for an example and does not imply that this level is used for any design or operational purposes.

In brief summary, the advantage of using the eutectic temperature to predict deposition potential is that it gives a lower limit at which particles will have liquid phases. It is well established that deposition of ash is controlled by the amount and nature of ash particles. Therefore, the determination of the amount of liquid phases present at a given temperature can be used as a method to predict deposition potential. It should be understood that the invention can be used with various fuels, for example, coal, wood ash and garbage ash.

While the invention has been described with reference to details of the illustrated embodiment, these details are not intended to limit the scope of the invention as defined in the appended claims.

What is claimed and desired to be secured by Letters Patent of the United States is:

1. Apparatus for predicting ash deposition on heated surfaces of a fuel burning combustion vessel in a combustion system comprising:
   means for obtaining an ash sample;
   means utilizing said obtained ash sample for identifying chemistry composition particle-by-particle;
   means for identifying equilibria phase diagram responsive to said identified chemistry composition of each said particle of said obtained ash sample; and
   means responsive to said identified equilibria phase diagram for identifying a eutectic temperature of each said particle of said obtained ash sample.

2. Apparatus as recited in claim 1 wherein said means for obtaining an ash sample include sampling means located in said fuel burning combustion system.

3. Apparatus as recited in claim 1 wherein said means for obtaining an ash sample include means for producing an ash sample from a predetermined fuel under predefined laboratory conditions.

4. Apparatus as recited in claim 1 wherein said means utilizing said obtained ash sample for identifying chemistry composition particle-by-particle include size analysis means for determining chemical composition of each said particle as a function of size.

5. Apparatus as recited in claim 1 wherein said means utilizing said obtained ash sample for identifying chemistry composition particle-by-particle include a computer controlled scanning electron microscope.

6. Apparatus as recited in claim 1 further includes means for controlling an operating temperature below the lowest identified eutectic temperature for the fuel burning combustion vessel in the combustion system.

7. Apparatus as recited in claim 1 further includes means for identifying a eutectic temperature distribution of said obtained ash sample and means responsive to said identified eutectic temperature distribution for identifying selected operational parameters of the combustion system.

8. A method of predicting ash deposition on heated surfaces of a fuel burning combustion vessel in a combustion system to determine operational parameters for the combustion system comprising the steps of:
   obtaining an ash sample;
   identifying characteristics of the obtained ash sample by a particle-by-particle analysis of the obtained ash sample;
   identifying equilibria phase diagram responsive to said identified characteristics of each said particle of said obtained ash sample; and
   identifying a eutectic temperature of each said particle of said obtained ash sample responsive to said identified equilibria phase diagram.

9. A method as recited in claim 8 wherein said step of identifying characteristics of the obtained ash sample includes the step of:
   identifying particle size; and
   identifying chemical composition of individual particles by computer controlled scanning electron microscopy.

10. A method as recited in claim 8 further comprising the step of:
    identifying an operating temperature below the lowest identified eutectic temperature in the fuel burning combustion vessel in the combustion system.

* * * * *